United States Patent [19]

Sjardijn et al.

[11] Patent Number: 5,093,441

[45] Date of Patent: Mar. 3, 1992

[54] POLYMERIZATION OF NORBORNENE DERIVATIVES

[75] Inventors: Willem Sjardijn; Johannes J. M. Snel, both of Amsterdam, Netherlands

[73] Assignee: Shell Oil Company, Houston, Tex.

[21] Appl. No.: 480,981

[22] Filed: Feb. 16, 1990

[30] Foreign Application Priority Data

Feb. 28, 1989 [GB] United Kingdom ............... 8904575

[51] Int. Cl.$^5$ .................. C08F 4/42; C08F 4/58; C08F 4/60; C08F 236/00; C08F 4/609
[52] U.S. Cl. .................. 526/126; 526/142; 526/150; 526/283
[58] Field of Search ........................... 526/90

[56] References Cited

U.S. PATENT DOCUMENTS 3,718,474  2/1973  Kolb et al. ............ 96/115 P
4,568,660  2/1986  Klosiewicz ............ 502/169

FOREIGN PATENT DOCUMENTS 142861  11/1984  European Pat. Off. .
61-293208  12/1986  Japan .
63-92625  4/1988  Japan .

*Primary Examiner*—Joseph L. Schofer
*Assistant Examiner*—Wu C. Cheng

[57] ABSTRACT

A process for the production of thermoset polymers comprising contacting at least one monomer of the formulae:

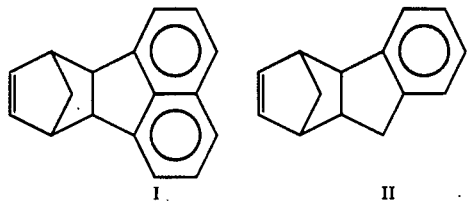

I.                                II with a metathesis catalyst system which comprises a tungsten catalyst and a tin or silicon hydride cocatalyst.

18 Claims, No Drawings

POLYMERIZATION OF NORBORNENE DERIVATIVES

BACKGROUND OF THE INVENTION

This invention relates to a process for the polymerization of bulky norbornene derivatives and to polymers obtained thereby. In one aspect, the invention relates to a process for the polymerization of specific bulky norbornene monomers to provide copolymers showing tailored product properties such as increased glass transition temperatures.

Extensive research efforts have been directed to the manufacture of polymers having high glass transition temperatures in combination with other desired properties. This appears, for example, from Japanese Patent Applications No. 61-293,208 and No. 63-092,625, U.S. Pat. No. 4,568,660, U.S. Pat. No. 3,718,474 and European Patent No. 0142861.

Japanese patent application No. 61-293,208 discloses the ring-opening polymerization of a copolymer in a reaction injection molding (RIM) process involving at least two norbornene-type monomers in the presence of a catalyst containing an inorganic tungsten compound and an activator to form a molded copolymer having an acceptable thermal resistance. Disclosed comonomers include tetracyclododecene, methyltetracyclododecene, dimethyltetracyclododecene, ethyltetracyclododecene and propyltetracyclododecene, and preferably at least one of 2-norbornene and dicyclopentadiene and at least one tetracyclododecene are used in a ratio of 5–8% by weight and 20–95% by weight, respectively, in a copolymerization catalyzed by a tungsten compound such as $WCl_6$ or $WOCl_4$ and an activator such as a dialkylaluminium monohalide, an aluminium sesquihalide, a trialkylaluminium and/or an aluminium trihalide as a metathesis catalyst system.

Japanese Patent Application No. 63-092,625 discloses moldings of crosslinked polymer obtained by polymerization in bulk, in the presence of a metathesis polymerization catalyst system, of a monomer mixture of 1:1 adducts obtained by Diels-Alder reaction between 3a,4,7,7a-tetrahydroindene and cyclopentadiene, or of these adducts and one or more other metathesispolymerizable monomers. However, it will be appreciated that the monomers as specified as MOHF and MBHI are bifunctional and provide a crosslinked polymer. More particularly in the examples as described only a TPA blend is used, comprising a 1:2:2 mixture of MOHG, MBHI and cyclopentadiene trimer (also being bifunctional), whereas no relatively high glass transition temperatures are mentioned. The highest glass transition temperature mentioned is 126° C., and average values are about 110° C. By post curing at 280° C., this glass transition temperature seems to be increased to at most 165° C., with an average value of about 140° C.

U.S. Pat. No. 4,568,660 discloses, in column 32, lines 58-68 and in column 33, lines 1-32, respectively, the addition of a comonomer having two or more strained, reactive double bonds that will open during the polymerization, in order to increase the number of crosslinks, or a comonomer which contains four or more rings so that rotation or movement of the resulting backbone will be more constrained, in order to provide higher Tg in the polymer. As examples of useful norbornene type monomers are mentioned 1:1 Diels-Alder adducts of cyclopentadiene with norbornene, norbornadiene and 1,5-cyclooctadiene, the adducts of cyclopentadiene with polyfunctional acrylates, such as trimethylolpropane triacrylate and the like, and the 2:1 adduct of cyclopentadiene with diallyl adipate. Substantial increases in the crosslink density (as measured by the degree of swelling of the copolymers) are reported with copolymers made from dicyclopentadiene (DCPD) and the cyclopentadiene adducts with norbornadiene, trimethylpropane triacrylate, ethylene glycol diacrylate and ethylene glycol dimethacrylate.

U.S. Pat. No. 3,718,474 discloses, in column 4, lines 52-58, the preparation of a copolymer of DCPD and acenaphthylene to be used in an exposure assembly for imagewise exposing a layer of a solid soluble polymer which is crosslinked to insoluble condition upon exposure to light.

European Patent No. 142,861 discloses a reaction injection molding method for making a crosslinked thermoset polymer containing units derived from DCPD, in the presence of an organoaluminium or alkylaluminium halide activator. In this method not more than 20% of the DCPD units are replaced by other polymerizable units and the catalyst is a pentavalent tantalum catalyst represented by the formula $Ta-Y_5$, wherein $-Y$ is a) a halide, b) an alkoxy having the formula $-O-R$ in which the organic radical R is a hydrocarbyl containing from 1 to 10 carbon atoms, c) an aryloxy having the formula $-O-Ar$, wherein the radical Ar is an aromatic radical containing from 1 to 3 aromatic rings, or d) an acyloxy having the formula $OOCR^1$, in which the organic radical $R^1$ is a hydrocarbyl containing from 1 to 10 carbon atoms. The other cycloolefin monomers are selected from norbornene, norbornadiene, cyclopentene, dimethanehexahydronaphthalene and dimethaneoctahydronaphthalene.

In spite of the efforts discussed above, there remains a growing need for an economical process for the manufacture of polymers showing tailored product properties such as an increased glass transition temperature which can be obtained without post-treatment of the polymer. It is therefore an object of the invention to provide such a process by using monomers having a specifically-adapted structure.

BRIEF SUMMARY OF THE INVENTION

According to the invention, a process is provided for the polymerization of norbornene derivatives, the process comprising contacting at least one monomer of the formulae:

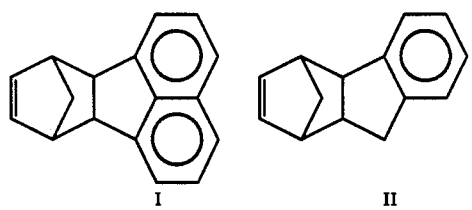

I                                    II with a ring-opening metathesis catalyst system comprising a tungsten catalyst and a tin or silicon hydride cocatalyst.

DETAILED DESCRIPTION OF THE INVENTION

The monomers I and II above may occur in principle in two isomeric forms, e.g., the endo and exo form, or mixtures thereof, both of which may be included in the monomer mixture to be polymerized. The polymerization of mixtures of monomers I and II may in general be carried out using mixtures in a wide range of proportions of the monomers, but preferably these mixtures will contain from 50 to 95% by weight of monomer I and from 5 to 50% by weight of monomer II, based on the total weight of both monomers.

The process of the present invention may also be applied to mixtures of monomers I and II and one or more additional comonomers which can be polymerized by ring-opening methathesis polymerization, such as dicyclopentadiene and norbornene derivatives, in amounts of up to 30% by weight, based on the weight of the total monomer mixture, preferably 5–20%.

The process enables the preparation of polymers exhibiting a desired increase of the glass transition temperature without post curing, and a further advantage of the process is in the ability to polymerize unpurified monomers I and/or II, as obtained in the Diels-Alder reaction referred to hereinafter.

The monomer of formula II is a novel compound and forms another feature of the invention.

The monomers according to formulae I and II may be prepared by starting from dicyclopentadiene (DCPD) and a dienophile. Monomer I may be prepared via a Diels-Alder addition by reacting DCPD, acenanaphthalene and hydroquinone under heating. Monomer II may be prepared by a Diels-Alder addition of DCPD and indene.

The catalyst component of the metathesis catalyst system is preferably a tungsten compound obtainable by combining a tungsten halide with a phenol derivative. The tungsten halide used for the preparation of the catalyst component may be a bromide or a fluoride, but is preferably a chloride, most preferably tungsten hexachloride or tungstenoxy tetrachloride (WOCl$_4$).

Preferably, the copolymerization process is carried out in the presence of a tungsten catalyst obtainable by combining a tungsten halide with a phenol derivative and a tin or silicon cocatalyst containing at least one hydrogen atom bound to the tin atom and/or the silicon atom.

In general, the phenol can be substituted with a bulky alkyl group at the positions ortho with respect to the hydroxyl group, or it can be a monocyclic halophenol in which the halogen atoms are attached to the aromatic nucleus. Among the halophenols, fluorophenols are preferred, but chlorophenols and bromophenols may be used. Very high reaction rates are obtained when polyfluorophenols are used. The highest rates of polymerization are obtained when the polyfluorophenol carries four or five fluorine atoms. Examples of such phenols are 2,3,4,5-tetrafluorophenol, 2,4,5,6-tetrafluorophenol and 2,3,5,6-tetrafluorophenol. Very good results have been obtained with 2,3,5,6-tetrafluorophenol and pentafluorophenol. An advantage of the use of such very active catalytic systems is that relatively small quantities thereof need be used.

High polymerization rates are also obtained when the phenol is a monocyclic phenol having a trihalomethyl substituent attached to the aromatic nucleus. The trihalomethyl substituent is preferably a trifluoromethyl group, but may be a trichloromethyl or tribromomethyl group. Very good results have been obtained with 3-trifluoromethylphenol. Other examples of such phenols are 2-trichloromethylphenol, 4-trifluoromethylphenol, 2-trifluoromethylphenol, 3-chlorodifluoromethylphenol, 3-dichlorofluoromethylphenol and 3-tribromomethylphenol.

According to a preferred embodiment of the present invention, the catalytic system is obtained by combining the following two components:

(1) a tungsten compound which is the reaction product of a tungsten halide and a para-trihalomethylphenol, the phenyl nucleus optionally being substituted by an alkyl group or halogen atom, and (2) one or more compounds of the formula:

wherein Q represents Sn or Si, in which $R^1$, $R^2$ and $R^3$ may represent an optionally substituted alkyl group of from 1 to 20 carbon atoms, an optionally substituted cycloalkyl group having in the range of from 3 to 6 carbon atoms in the cycloalkyl ring, or an optionally substituted phenyl group, and in which $R^1$ and $R^2$ may each also represent hydrogen.

Component 1 may be prepared in the presence of a suitable solvent. Examples of such solvents are cyclopentane, cyclohexane, benzene, toluene, o-, m- and p-xylene, chlorobenzene and 1,2-dichlorobenzene. According to a more preferred embodiment, the component 1 is dissolved in at least one of monomers I and II or DCPD, if used as additional comonomer.

Suitably, a molar ratio of phenol to tungsten in the range of from 1:1 to 10:1 and preferably 3:2 to 3:1 is used. The preparation of component 1 may take place by suspending a tungsten halide in the solvent and adding the phenol to the resulting suspension, stirring the reaction mixture and blowing a stream of a dry inert gas, for example nitrogen, through the mixture to remove the hydrogen halide which is formed.

Component 2 is preferably a tin compound of the general formula I in which $R^1$, $R^2$ and $R^3$ each represent a $C_{1-10}$, preferably $C_{2-4}$, alkyl group or phenyl, when Q represents tin. At least two of the symbols represent alkyl or phenyl when Q represents silicon. Examples of suitable tin compounds are tripropyltinhydride, tripentyltinhydride, tributyltinhydride, methyldicyclohexyl tinhydride, cyclopentyldimethyltinhydride, trioctyltinhydride, triphenyl tinhydride and phenyldimethyltinhydride, of which tributyltinhydride is preferred. Examples of suitable silicon compounds are dibutylsilane, triethylsilane, trihexylsilane, dipropylsilane, dipentylsilane, diphenylsilane, dicyclohexylsilane, dicyclopentylsilane and dioctylsilane. Examples of substituents in $R^1$, $R^2$ and $R^3$ are alkoxy groups having in the range of from 1 to 20 carbon atoms and chlorine and fluorine atoms.

The process according to the present invention can be carried out at a molar ratio of tungsten to monomer I and/or II and a molar ratio of tin and/or silicon compound of the general formula I to tungsten which are not critical and may vary within wide ranges. Preferably, the former ratio is in the range of from 1:20,000 to 1:100 and in particular 1:1,000 to 1:10,000, and the latter ratio is in the range of from 15:1 to 1:1, preferably 12:1 to 3:1.

The technical grade may contain, for example, at least 83% by weight of pure monomer I or II. An advantage of the use of such technical grades is that they are usually liquid at ambient temperature, say at 20° C.

Commercially, the starting dicyclopentadiene to be used for manufacturing the monomers I or II or to be copolymerized is usually available in the endo form, but, if desired, the exo form or mixtures of the endo and exo form may be used.

Generally, the polymerization takes place in bulk, but catalyst components 1 and 2 may be dissolved in a small amount of solvent, such as toluene. It is preferred to use, however, monomer I and/or II or DCPD, if any, as a solvent for at least one of the two components.

A preferred method for the polymerization of the monomer mixture is to allow contact between a stream of component 1 and a stream of component 2, whereby at least one of the streams has been admixed with the monomer I and/or II or DCPD prior to the polymerization, and to polymerize the comonomers. For example, it is possible to dissolve component 1 in monomer I or II and/or DCPD and either to dissolve component 2 in the monomer I or II and/or DCPD or in another solvent or to use the activator without any solvent. After both streams have been contacted with each other, the resulting mixture is preferably injected or poured into a mold where polymerization of the monomer mixture takes place.

Component 1 and component 2 may be stored in one of the monomers for some time, provided that the monomer contains not more than a few parts per million (ppm) by weight of water. Component 2 is storable in the monomer for one to two months without losing its activity. These stock solution are preferably mixed with the desired predetermined amount of selected monomer(s).

It will be appreciated that starting reaction mixtures or components thereof, comprising at least one of the monomers I and/or II, the catalyst component (1) or (2) and optionally DCPD and/or another solvent, also form an aspect of the present invention. The reaction mixture components or streams may also include an additional solvent.

The process according to the present invention may be carried out in the presence of auxiliary materials, for example fillers, fibers, anti-oxidants, tougheners, stabilizers, pigments and plasticizers.

The catalytic system used in the process is specifically of interest for reaction injection molding or casting. Because of the low viscosity of the monomers/catalyst system mixture, the polymerization is very suitable for large castings with intricate molds. The process is usually carried out at an average polymerization temperature in the range of from 50° C. to 170° C. It is a favorable feature of the present invention that the components 1 and 2 of the catalytic system are very stable.

A further advantage of the process of the present invention resides in the fact that the polymer obtained by the process need not be subjected to a heat treatment at a temperature in the range of from 200° C. to 300° C. for times of an hour or longer to increase the glass transition temperature of the polymer from a starting value of 125° C. to 175° C., which advantage renders the polymer more useful and saves energy costs.

The process according to the invention allows quantitative polymerization, the final polymer being free from starting monomers. For this reason the polymer is free from odor and can be used for a large number of applications, for example, for (a) structural composites, for example in the automotive industry, and building industry and (b) application in the electrical industry, for example in printed circuit boards.

EXAMPLE 1 a) Synthesis of 5,6-acenaphthene-norbornene (monomer I)

A mixture of 164 g of DCPD (1.2 mol), 168 g of acenaphthylene (1.1 mol) and 4 g of hydroquinone was heated in an autoclave under nitrogen at 150°-160° C. for 16 hours and the resulting mixture was cooled and filtrated. The remaining solution was distilled in vacuo to give a yellow liquid, which later crystallized. The yield was about 120 g endo 5,6-acenaphthenenorbornene (0.55 mol). This synthesis was carried out according to R. Baker and T. J. Mason, J. Chem. soc. (c) (1970) 596. The obtained addition product could be identified by the following characteristic NMR signals:

$^1$H NMR (CDCl$_3$) (endo) $\delta$1.65-1.8 ppm (2H); $\delta$3.25 ppm (2H); $\delta$4.1 ppm (2H); $\delta$5.4 ppm (2H); and $\delta$7.2-7.7 ppm (6H); (exo), $\delta$0.8-1.4 ppm (2H); $\delta$2.9 ppm (2H); $\delta$3.6 ppm (2H); $\delta$6.35 ppm (2H) and $\delta$7.2-7.7 ppm (6H).
$^{13}$CNMR (CDCl$_3$) (endo) $\delta$45.7; $\delta$50.5; $\delta$50.8; $\delta$119.0; $\delta$122.6; $\delta$127.4; $\delta$131.1; $\delta$133.7; $\delta$141.6 and $\delta$146.4.

b) Preparation of catalyst 1

2 g of WCl$_6$ was weighed in a 100 ml dried serum cap bottle and dissolved in 40 ml of dried toluene under a dry nitrogen blanket. 1.73 ml of dried 2,6-diisopropylphenol was added slowly at 100° C. The evolved HCl was collected in an excess of aqueous sodium hydroxide solution. The reaction mixture was kept for 4 hours at 100° C.

c) Polymerization 0.022 g of catalyst 1 was introduced in a 100 ml serum cap bottle, together with 10 g of 5,6-acenaphthenenorbornene as obtained under a). This mixture was thoroughly homogenized at room temperature and 37.5$\mu$ of tributyl tin hydride was added at ambient temperature by means of a hypodermic syringe. The bottle was shaken thoroughly and placed in an oil bath of 90° C. An exothermic polymerization was observed. A maximum temperature of 135° C. within 5 minutes from initiation was observed. The reaction mixture was kept at 90° C. for one hour. A polymer showing a Tg$\simeq$135° C. was recovered.

EXAMPLE 2 a) Preparation of catalyst 2

4 g of WCl$_6$ was weighed in a 100 ml dried serum cap bottle and dissolved in 20 ml of dried toluene under a dry nitrogen blanket. A solution of 6.6 g dried 2,6-ditertbutyl-4-methylphenol (Ionol) in 20 ml of dried toluene was added slowly at 95° C. The evolved HCl was collected in an excess of aqueous sodium hydroxide solution. The reaction mixture was kept for 4 hours at 95° C. The product was isolated by evaporation of the solvent.

b) Polymerization 0.07 g of catalyst 2 was introduced in a 100 ml serum cap bottle together with 7 g of 5,6-acenaphthenenorbornene as obtained according to example 1a. This mixture was thoroughly homogenized at room temperature and 37.0$\mu$ of tributyltinhydride was added at ambient temperature by means of a hypodermic syringe. The bottle was shaken throughly and placed in an oil bath of 90° C.

An exothermic polymerization was observed for which a maximum temperature of 135° C. after 11 minutes from initiation was recorded.

EXAMPLE 3 a) Synthesis of 5,8-methylene-5a,8a-dihydrofluorene (monomer II) in one reactor

A mixture of 58.5 ml indene (0.5 mol), 66.1 ml of dicyclopentadiene (0.5 mol) and 2 g of hydroquinone was heated during 18 hours on 150° C. to 160° C. The reaction mixture was cooled to ambient temperature and filtered to remove the hydroquinone. The filtrate was distilled under vacuo and the norbornene derivative was recovered as a colorless liquid at 68° C. at 1 mbar in a yield of about 60 g (66%). The obtained norbornene derivative could be identified by the following characteristic NMR signals:

PMR (CDCl$_3$): $\delta$0.5-4.0 ppm (8H); $\delta$5.6 ppm (1H); $\delta$5.95 ppm (1H) and $\delta$6.9-7.2 ppm (4H); $^{13}$CNMR (CDCl$_3$): $\delta$34.6; $\delta$41.8; $\delta$46.6; $\delta$46.9; $\delta$50.7; $\delta$53.7; $\delta$124.1; $\delta$124.3; $\delta$125.7; $\delta$126.2; $\delta$133.0; $\delta$136.3; $\delta$145.1 and $\delta$145.7 ppm;

b) Polymerization of 5,8-methylene-5a,8a-dihydrofluorene (monomer II)

In a reaction bottle were introduced 22 mg of catalyst 1 and 9.0 g of monomer II under nitrogen. This mixture was thoroughly homogenized at ambient temperature and subsequently a solution of 40 mg of tributyl tinhydride in 1 ml of monomer II was added at ambient temperature by means of a hypodermic syringe. The bottle was shaken thoroughly and placed in an oil bath at 90° C.

An exothermic polymerization was observed and maximal temperature jump occurred to about 170° C. within 5.5 to 6 minutes. The reaction mixture was kept at 90° C. for an additional hour. The polymer obtained showed a Tg of 175° C.

EXAMPLE 4

In the same way as described in Example 3b) a polymerization was carried out by using catalyst 2 and monomer II under nitrogen. The polymer obtained showed a Tg of 175° C.

EXAMPLE 5 a) Preparation of catalyst 3

WCl$_6$ (1.73 mmol) was suspended in dried cyclopentane (5 ml) at ambient temperature under a dry nitrogen blanket. Para-trifluoromethylphenol (3.5 mmol) in cyclopentane (20 ml) was added. After completion of the reaction the catalyst was isolated by evaporation of the solvent.

b) Polymerization

A 30 ml serum cap bottle was charged with 22 mg of the catalyst prepared in Example 3a, and a dried mixture of 5 g of monomer I as obtained according to example 1a, and 5 g of monomer II as obtained according to example 3a were added under a dry nitrogen blanket. Subsequently tributyltinhydride (80 mg) was added, resulting in an exothermic polymerization. Two minutes after introduction a maximum temperature of 150° C. was reached.

EXAMPLE 6

In a 30 ml serum cap bottle, 22 mg of catalyst 3 obtained according to example 5 was mixed with 10 g of monomer I, as obtained according to example 1a, under a dry nitrogen blanket. Subsequently triethylsilane (0.15 ml) was added. The reaction mixture was placed in an oil bath of 90° C. resulting in an exothermic polymerization. After 5 minutes, a maximum temperature of 140° C. was recorded.

EXAMPLE 7

In the same way as described in example 6, a polymerization of 10 g monomer II was carried out, using 60 mg diphenylsilane instead of triethylsilane.

EXAMPLE 8

In a 30 ml serum capped bottle 22 mg of the catalyst prepared in Example 5 and a dried mixture of 5 g of monomer I as obtained according to Example 1a, and 5 g of monomer II as obtained according to Example 3a were added under a dry nitrogen blanket. Subsequently 0.15 ml triethylsilane reaction mixture was placed in an oil bath of 90° C. resulting in an exothermic polymerization. After 6 minutes a maximum temperature of 140° C. was recorded.

We claim:

1. A process comprising contacting at least one monomer of the formulae:

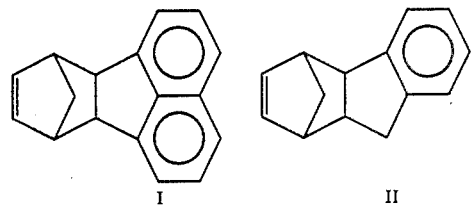

I   II with a ring-opening metathesis catalyst system comprising a tungsten catalyst which is the reaction product of a tungsten halide and a phenol and a cocatalyst selected from triorgano tin hydrides and silicon hydrides, under conditions effective for polymerization of said at least one monomer.

2. The process of claim 1 in which the catalyst component is the product of reacting tungsten hexachloride or tungstenoxy tetrachloride with a phenol.

3. The process of claim 1 in which a mixture of monomers I and II containing from 50 to 95% by weight of monomer I and from 5 to 50% by weight of monomer II, based on the total weight of both monomers, is polymerized.

4. The process of claim 1 in which the polymerization process is carried out using monomer mixtures of monomers I and II containing up to 30% by weight of dicyclopentadiene, calculated on the weight of the total monomer mixture.

5. The process of claim 4 in which a monomer mixture containing 5-20% by weight of dicyclopentadiene is used.

6. The process of claim 1 in which catalyst component 1 is the reaction product of a tungsten halide and a monocyclic phenol having a trihalomethyl substituent attached to the aromatic nucleus.

7. The process of claim 6 in which the trihalomethyl-substituted phenol is selected from the group consisting of 3-trifluoromethylphenol, 2-trichloromethylphenol, 4-trifluoromethylphenol, 2-trifluoromethylphenol, 3- chlorodifluoromethylphenol, 3-dichlorofluoromethylphenol and 3-tribromomethylphenol.

8. The process of claim 1 in which the metathesis catalyst system is the product of combining the following components:
   (1) a tungsten compound which is the reaction product of a tungsten halide and a substituted or unsubstituted para-trihalomethylphenol and
   (2) one or more compounds of the formula:

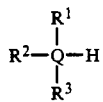   I in which Q represents Sn or Si, $R^1$, $R^2$ and $R^3$ are independently selected from $C_{1-20}$ alkyl, $C_{3-6}$ cycloalkyl and phenyl, and $R^1$ and $R^2$ are additionally selected from hydrogen.

9. The process of claim 8 in which the catalyst component 1 is dissolved in a solvent comprising at least one of monomers I and II.

10. The process of claim 8 in which the molar ratio of phenol to tungsten is within the range of about 3:2 to about 3:1.

11. The process of claim 8 in which catalyst component (2) is selected from the group consisting of tripropyltinhydride, tripentyltinhydride, tributyltinhydride, methyldicyclohexyltinhydride, cyclopentyldimethyltinhydride, trioctyltinhydride, triphenyltinhydride and phenyldimethyltinhydride.

12. The process of claim 8 in which catalyst component (2) is tributyltinhydride.

13. The process of claim 8 in which catalyst component (2) is selected from the group consisting of dibutylsilane, triethylsilane, trihexylsilane, dipropylsilane, dipentylsilane, diphenylsilane, dicyclohexylsilane, dicyclopentylsilane and dioctylsilane.

14. The process of claim 8 in which the molar ratio of tungsten to dicyclopentadiene monomer is within the range of 1:1,000 to 1:10,000.

15. The process of claim 8 in which the molar ratio of catalyst component (2) to tungsten is within the range of about 12:1 to about 3:1.

16. A composition comprising at least one of compounds represented by formulas I and II and

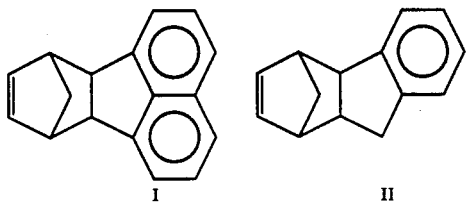

a tungsten halide.

17. The composition of claim 16 which further comprises a triorganotin hydride.

18. A polymeric product of the process of claim 1 comprising a major portion of polymerized units derived from at least one of monomers I and II.

* * * * *